United States Patent
Zhang et al.

(10) Patent No.: US 9,447,198 B2
(45) Date of Patent: *Sep. 20, 2016

(54) METHOD FOR EXTRACTING POLYSACCHARIDES FROM HIGHER PLANTS AND FUNGI THROUGH MICROWAVE CHEMICAL TREATMENT

(71) Applicant: Shenyang Kesi High-Technology Co, Ltd., Shenyang, Liaoning Province (CN)

(72) Inventors: Jinsong Zhang, Shenyang (CN); Mingtian Li, Shenyang (CN); Zhiyu Liu, Shenyang (CN); Lei Xu, Shenyang (CN)

(73) Assignee: SHENYANG KESI HIGH-TECHNOLOGY CO. LTD., Shenyang, Liaoning Province (CN)

( * ) Notice: Subject to any disclaimer, the term of this patent is extended or adjusted under 35 U.S.C. 154(b) by 35 days.

This patent is subject to a terminal disclaimer.

(21) Appl. No.: 14/355,531

(22) PCT Filed: Nov. 1, 2012

(86) PCT No.: PCT/CN2012/083934
§ 371 (c)(1),
(2) Date: Apr. 30, 2014

(87) PCT Pub. No.: WO2013/067897
PCT Pub. Date: May 16, 2013

(65) Prior Publication Data
US 2014/0309414 A1  Oct. 16, 2014

(30) Foreign Application Priority Data
Nov. 7, 2011 (CN) .......................... 2011 1 0348823

(51) Int. Cl.
*C08B 37/00* (2006.01)
*C08H 8/00* (2010.01)

(52) U.S. Cl.
CPC ......... *C08B 37/0003* (2013.01); *C08B 37/006* (2013.01); *C08H 8/00* (2013.01)

(58) Field of Classification Search
CPC .... C08B 37/0003; C08B 37/006; C08H 8/00

USPC .......................... 514/123.1; 536/123.1, 124
See application file for complete search history.

(56) References Cited

FOREIGN PATENT DOCUMENTS

| CN | 1580079 | | 2/2005 |
|---|---|---|---|
| CN | 1880342 | | 12/2006 |
| CN | 101074269 | | 11/2007 |
| CN | 101240036 | | 8/2008 |
| CN | 101993501 A | * | 3/2011 |
| CN | 102093598 | | 6/2011 |
| CN | 102268100 A | * | 12/2011 |
| CN | 102391387 | | 3/2012 |

OTHER PUBLICATIONS

Liu et al.; CN 102268100 A; Dec. 7, 2011 (Machine—English Translation).*
Derwent abstract of Liu et al.; CN 102268100 A; Dec. 7, 2011 (abstract sent).*
Mao et al.; CN101993501 A; Mar. 30, 2011 (Machine—English Translation).*
International Search Report issued in PCT Application No. PCT/CN2012/083934.

* cited by examiner

*Primary Examiner* — Shaojia Anna Jiang
*Assistant Examiner* — Michael C Henry
(74) *Attorney, Agent, or Firm* — Lucas & Mercanti, LLP

(57) ABSTRACT

This invention relates to a field of pharmaceutical chemistry, relates to a process of extracting high water soluble polysaccharides from higher plants or fungi. The present invention discloses a process of extracting higher plants and fungi polysaccharides based on a microwave chemistry method, comprising: putting the residue or pulverized higher plants and fungi after being degreased by an organic solvent into a microwave reaction chamber to react with an acid solution; and then distilling to remove excess acid or washing with organic solvent to remove the acid; adding water solution for extraction, subjecting the extracting solution after concentration to alcohol precipitation, separating precipitates aka polysaccharides therefrom.

The present invention has significant advantages like fast processing rate, high polysaccharides yield, low organic acid consumption and efficient and easy to recycle, low water consumption, low power consumption, etc., and obtained polysaccharides have high yield and purity, good water solubility, and good biological activity.

44 Claims, 1 Drawing Sheet

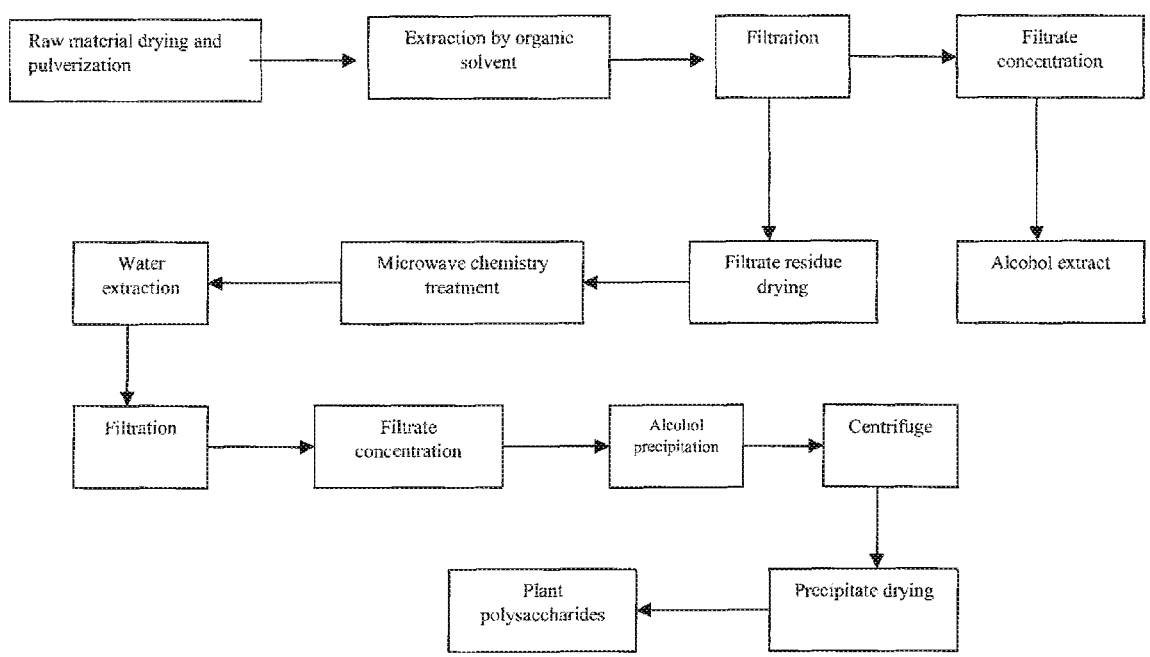

METHOD FOR EXTRACTING POLYSACCHARIDES FROM HIGHER PLANTS AND FUNGI THROUGH MICROWAVE CHEMICAL TREATMENT

CROSS-REFERENCE TO RELATED APPLICATIONS

This application is a U.S. national stage of PCT/CN2012/083934 filed on Nov. 1, 2012 which claims the benefit of priority from Chinese Patent Application No. 201110348823.X filed Nov. 7, 2011, the contents of each of which are incorporated herein by reference.

TECHNICAL FIELD

This invention relates to a field of pharmaceutical chemistry, relates to a process of preparing water soluble polysaccharides using higher plants and fungi as raw material, and particularly relates to a process of extracting higher plants and fungi polysaccharides based on a microwave chemistry method.

DESCRIPTION OF BACKGROUND

Polysaccharides are natural macromolecular compounds comprising of a plurality of monosaccharide molecules bonded via glycosidic bonds, and are one of the fundamental substance of life. In recent twenty years, with the development of molecular biology and cell biology, it was discovered that polysaccharides have a variety of biological functions, polysaccharides and their conjugates are involved in the life activities of cells, such as cell-specific recognition, component of a variety of antigens and drug receptors on cell surface, activation of immune cells. Thus polysaccharides arouse great research interests.

Polysaccharides of higher plants and fungi have a long history of applications in China, and have also very rich resources. They has become a focus and a research hotspot. Modern pharmacological studies indicate that these two types of polysaccharides have very important and special physiological activities, and play a clear role in promoting immunity, anti-bacterial, anti-viral, anti-parasitic, anti-tumor, anti-radiation, anti-thrombotic, anti-clotting, anti-aging, inflammation, lowing blood fat and improving animal fertility and other aspects. Moreover, most of the polysaccharides have no direct cytotoxicity, and can be used in long-term. Polysaccharides of higher plants and fungi have currently become one of the most promising health care resources.

Bioactivity of polysaccharides largely determines the application value of polysaccharides. Constituent components, composition and spatial conformation, molecular weight and molecular weight distribution, water-solubility of polysaccharides are the main factors affecting biological activities of polysaccharides. Numerous studies show that the molecular weight of active polysaccharides is one of the necessary conditions for having biological activity. Greater molecular weight of polysaccharide, greater apparent volume of the molecule, which does not benefit polysaccharides to go across multiple membrane barriers into play in vivo biological activities. Water-soluble polysaccharides closely related to the molecular weight thereof is another important condition for playing its biological activities.

The very complex structure of polysaccharides causes the synthesis thereof extremely difficult. Currently, all active polysaccharides are extracted from natural products. Higher plants polysaccharides and fungi polysaccharides are extracted and isolated from different plants or different parts of the same plant, and fungal sporocarp, mycelium and mycelial fermentation broth.

There is no commonly accepted, effective, unified separation method of extracting polysaccharides. Existing processes can generally be summarized as water extraction, acid extraction, alkali extraction, salt extraction and enzyme supplementary extraction. These methods have significant shortcomings in the aspects of polysaccharide extraction efficiency, cleanness of the production process, energy and material consumption, or polysaccharide structure modification, etc. The technology value of obtained polysaccharide products is not very high (particularly in: polysaccharide's low purity, poor water solubility, broad molecular weight distribution, etc.), which limits the high value-added applications of polysaccharides. Specifically, the existing polysaccharide extraction methods have the following problems:

Water extraction generally is time-consuming, has high energy consumption, uses a large amount of extracting solvent, and has low polysaccharide extraction yield.

It is hard to control the amount of inorganic strong acid, strong base and reaction time in acid alkali extraction, which easily causes the activity of polysaccharide molecules be destroyed, and even makes polysaccharides generate pigment molecules of small molecular weight burdening the subsequent bleaching work. Moreover, after the end of the reaction, neutralization or dialysis to acid, alkali solution much be quickly done, otherwise it will cause products contaminated, and increase insecurity of the products for food and healthcare products. In addition, the use of non-degradable inorganic acid or base likely causes serious environmental pollution in large scale industrial production.

The enzyme used in enzyme assisted extraction is generally expensive, often is easily inactivated, and has other shortcomings like short life and low purity. In enzymatic hydrolysis process, the optimal temperature is often in a very small range, and slight fluctuations of reaction conditions may cause the enzyme activity significantly decrease. Therefore, enzyme extraction has relatively high requirements on experimental conditions, and even requires very complicated pretreatment to extraction raw materials. Enzyme extraction technology still needs further research to be used for the industrial extraction of polysaccharides.

There are many reasons for these difficulties. In general, higher plants, fungi active polysaccharides have large molecular weight, and poor water-solubility. They have low content in the plant materials, complex distribution condition and distribution status, wherein some are in free state, some are bonded with macromolecules like proteins and hemicellulose to form complex conjugates, some are in the cytoplasm, some are in the cell wall. Main components of plant cell walls are cellulose, and other substances including hemicellulose, pectin, lignin, etc. Cellulose has supermolecular stable structure of high degree crystalline region, which is difficult to be hydrolyzed. Common extraction method can only apply a large number of solvent for long time immersion, so that the full expansion of the plant cell wall will make compact structure becomes loose and reduce the mass transfer resistance of the active ingredients diffusing from the cell to the solvent. Thus, conventional methods have high energy and material consumption, utilize polysaccharides in a free state in plants, but have poor extraction effects on polysaccharide wrapped in call wall or bonded in certain forms with other macromolecules.

CN03133778.3 patent application discloses a method of fully releasing active ingredients of lucid ganoderma spores.

The method puts lucid ganoderma spore into a microwave reaction chamber, adds an organic acid solution, conducts microwave treatment after mixing, then vacuum distills to remove the organic acid, and finally uses conventional water extraction, alcohol precipitation method to extract crude lucid ganoderma spore polysaccharides from microwave treated lucid ganoderma spore. Compared with conventional extraction methods, the method exponentially increases the yield of polysaccharides (above 3 times), but has the following main problems. First, only using vacuum distillation rather than further washing with an organic solvent to remove residual acid after the microwave treatment causes the resulting product having a high content of residual acid. And in the removal of oxalate acid, calcium precipitation method is adopted, which first washes off oxalic acid from the spores with water along with dissolved polysaccharide; when calcium ions are added to form calcium oxalate precipitates, a small amount of polysaccharides would be wrapped and lose. Second, the mechanism is based on that microwave enhanced reaction between organic acid and chitin and glial in the cell wall of lucid ganoderma spore, as to reduce restrictions of these substances on polysaccharide release, but does not recognize the importance of breaking the chemical bonding between polysaccharides and protein, cellulose, hemicellulose, and chitin, and degradation of polysaccharides on improving the yield and water-solubility of polysaccharides.

U.S. Pat. No. 8,110,677 discloses a method of microwave extraction of active polysaccharides from artemisia songarica schrenk. The method has technical defects like using a large amount of extraction solvent (water of 30-50 times is needed), and that enzymolysis is needed after obtaining polysaccharides, wherein enzymolysis causes many constraints, such as long reaction time (10-12 hours in the patent), and removal of enzyme after the reaction (n-butanol and chloroform extraction in the patent).

CN200510026889.1 patent application discloses a method of microwave extraction of astragalus polysaccharides. The method uses an inorganic strong acid (hydrochloric acid or sulfuric acid), an inorganic strong base (potassium hydroxide, sodium hydroxide, ammonia), wherein the inorganic strong acid and inorganic strong base cause serious equipment corrosion, are difficult to be recycled, and easily cause environment pollution, and the amount of inorganic acid is still relatively large. The hydrolysis of polysaccharides by the inorganic acid or base is mainly performed by adjusting the acid concentration, they only have acids, alkaline degradation and bond cleaving effects on polysaccharides, and the hydrolysis of polysaccharides under inorganic strong acid and strong base conditions is difficult to control, and cannot achieve the protective effects on polysaccharide molecules.

Therefore, there is a need to further develop a new method to extract active polysaccharides from higher plants or fungi.

SUMMARY OF THE INVENTION

To overcome above technical defects, the present invention provides a novel process of extracting higher plants and fungi polysaccharides via a microwave chemistry treatment. In the process of the present invention, a small amount of acids is used, raw materials are evenly heated, extraction yield of polysaccharides is high, and polysaccharides have high water solubility and good activity.

The process of the present invention of extracting higher plants and fungi polysaccharides based on a microwave chemistry comprises the following steps:

1) treating pulverized higher plants and fungi with an organic solvent to remove liposoluble components thereof to obtain higher plants and fungi residue; or directly using pulverized higher plants and fungi;
2) putting the residue or pulverized higher plants and fungi obtained in step 1) into a microwave reaction chamber, adding an acid solution of a mass concentration of 5% to 99%, conducting reaction of the mixer for 5-120 mins at a microwave power of mass power density of 1 kilowatt per kilogram of material—10 kilowatts per kilogram of material under a work pressure of 20 mmHg-760 mmHg; optionally concentrating the mixer to remove the organic acid, and then washing with an organic solvent to further remove residual acid;
3) adding water solution of 5-15 times into the product obtained from step 2), conducting water extraction and filtration, subjecting the filtrate solution after concentration to alcohol precipitation, preferably adding alcohol in the solution to an ethanol content of 70%-85%, to separate precipitates, i.e. polysaccharides products.

In the process of the present invention, as one of the embodiments, when the organic acid in the acid solution used in step 2) is a non-volatile acid, there is no need to remove the acid by concentration after the microwave reaction is completed; when the organic acid used is volatile acid, after the microwave reaction is completed, concentration is conducted to remove the acid, and then washing with an organic solvent is conducted to remove a small amount of residual acid.

Wherein, the concentration in step 2) can be done using common methods in the art, preferably by microwave heating under reduced pressure, and then washing with an organic solvent is conducted to remove the residual acid.

In the process of the present invention, as one of the embodiments, the application method of the microwave power in said step 2) is a continuous microwave mode or a combination of continuous microwave and pulse microwave modes until the acid solution refluxes, the microwave is kept for 5 min-120 min after the reflux starts; wherein, in case of using the combination of continuous microwave and pulse microwave, the continuous microwave irradiation is first used until the acid solution refluxes, and then is switched to pulse microwave for 5 min-120 min;

As one of the preferred embodiments, in said step 2), in case of continuous microwave, mass power density is 1 kilowatt per kilogram of material-5 kilowatts per kilogram of material; in case of pulse microwave, mass power density is 2 kilowatts per kilogram of material-10 kilowatts per kilogram of material, the duty ratio is A/B, where A=1 sec-100 sec, B=1 sec-100 sec.

In the process of the present invention, a microwave reaction chamber common in the art can be used for the microwave reaction, which is either a traveling wave microwave reaction chamber or a resonant microwave reaction chamber.

In the process of the present invention, as one of the embodiments, the acid solution in said step 2) is an organic acid or a mixed solution of an organic acid and an inorganic acid; wherein the organic acid solution is selected from oxalic acid, formic acid, acetic acid, or propionic acid; further preferably, a weight percentage concentration of the oxalic acid is 5% to 50%, preferably 10%-35%; a weight percentage concentration of the formic acid is 10%-99%, preferably 30-85%; a weight percentage concentration of the acetic acid is 10%-99%, preferably 60-95%; or a weight percentage concentration of the propionic acid is 10%-99%, preferably 70-95%.

In the process of the present invention, as one of the embodiments, in the mixed solution of organic and inorganic acids used in said step 2), the concentration of the organic acid in the mixed solution is above defined concentration of the organic acid; and mass percentage concentration of the inorganic acid is 0.1%45%; further preferably, the inorganic acid is selected from hydrochloric acid, sulfuric acid, nitric acid or phosphoric acid.

Above mentioned inorganic acid solution can be commercially purchased, and then used to prepare the corresponding concentration of the organic-inorganic mixed acid solution using conventional methods in the art. For instance, hydrochloric acid of a concentration of 36% is added to the organic acid to reach the corresponding concentration.

In the process of the present invention, as one of the embodiments, in the step 2), the ratio of the residue or pulverized higher plants and fungi obtained in step 1) to the amount of the acid solution is 5/1-1/5; one skilled in the art can adjust by adding or reducing within above range, as to ensure sufficient wetting of the materials, but cannot use too excessive acid solution, which otherwise causes difficult post processing and consumes too much energy.

In the process of the present invention, as one of the embodiments, the organic solvent used in said step 2) is selected from methanol, ethanol, propanol or acetone.

In the process of the present invention, said step 2) is a microwave chemistry treatment of raw materials, wherein the function of the microwave chemistry treatment mainly are: cleaving various bonds between polysaccharides and organic macromolecules including proteins, cellulose, hemicellulose, lignin, chitin of cell walls of higher plants and fungi, to convert bond polysaccharides to free polysaccharides as to increase the extraction yield in later process; second, moderately cutting the glycosidic bonds of the macromolecular polysaccharides, to achieve partial degradation thereof as to increase the water solubility thereof; and organic acid is used as in addition to H+ ions's degradation effects on polysaccharides, organic acid radical ions can protect polysaccharide molecules by forming hydrogen bonds with hydroxyl groups of the polysaccharides.

The process of the present invention, the pretreatment methods of higher plants, fungi raw material in said step 1) include, but are not limited to, the following two methods: 1) flowers, leaves, seeds, barks, fruits, roots or tubers of said higher plants, or mycelium or sporocarp of fungi raw materials are dried, decontaminated, and mechanically pulverized to be used as raw material for the next step; or 2) flowers, leaves, seeds, barks, fruits, roots or tubers of said higher plants, or mycelium or sporocarp of fungi raw materials are dried, decontaminated, mechanically pulverized, and extracted with an organic solvent to remove liposoluble active substances thereof including volatile oils, flavonoids, triterpenoids or saponins, and the residue of the extraction after drying is used as raw material for the next step.

In the process of the present invention, as one of the embodiments, the organic solvent used to treat pulverized higher plants or fungi in said step 1) is petroleum ether, methanol, ethanol, propanol or ethyl acetate. One skilled in the art can determine the amount of the organic solvent to be used according to the present invention and common knowledge in the art, which is to enable the materials be immersed, and generally is 6-8 times of the volume thereof, so as to remove liposoluble active substances thereof including but not limited to volatile oils, flavonoids, triterpenoids or saponins.

In the process of the present invention, as one of the embodiments, the alcohol used in said step 3) is ethanol.

In the process of the present invention, the active polysaccharides obtained by using the process of the present invention may be further refined by using conventional refining methods in the art. The refining includes, but is not limited to: the obtained crude polysaccharides product is added to distilled water of 10-20 times of its weight, sufficiently stirred to dissolve, and centrifuged at a RPM of 4000-8000 r/min for 10-30 minutes, the precipitate is discarded and the supernatant is dialyzed in distilled water for 24 h, the dialysate is directly lyophilized to obtain polysaccharides of high purity, or the dialysate is concentrated to ⅕ of the original volume thereof, and then added with ethanol until there is no precipitation in the solution, centrifuged and the precipitates are dried to obtain refined polysaccharides.

In the process of the invention, higher plants used to extract active polysaccharides by the process of the present invention include but are not limited to, as raw materials, flowers, leaves, seeds, barks, fruits, roots or tubers of *astragalus*, wolfberry, ginko leaf, *papaya*, honeysuckle, Chinese *angelica*, orange peel, *ephedra sinica*, *ligusticum chuanxiong hort*, *acorus gramineus*, garlic, sharpleaf galangal fruit, *angelica*, Chinese mugwort leaf, *asarum, cistanche, elaeagnus angustifolia, eucalyptus* leaf, *cordata, ligustrum lucidum, notopterygium, ginseng, panax pseudoginseng, sarcandra glabra, plantago, polygonum orientale* fruit, *daphne genkwa*, bergamot, white mulberry root-bark, mistletoe, *scutellaria baicalensis, epimedium*, tea leaf, *rhodiola, aloe*, oat, konjac, yam, *gastrodia elata, radix bupleuri* or *acanthopanax*; fungi includes but are not limited to fungal sporocarp or mycelium of lucid *ganoderma, exidia auricula judae*, mushrooms, polyporus, tremella, maitake, *poria*, rainbow conk, *hericium erinaceus* or *cordyceps sinensis*; as one of the preferred embodiments, the higher plants is *astragalus*, wolfberry, yam, gingko leaf, *panax pseudoginseng, plantago, gastrodia elata, eucommia ulmoides, salvia* or kudzu; the fungi is lucid *ganoderma, poria, exidia auricula judae*, or mushrooms.

In the process of the present invention, as one of the embodiments, the present invention further provides a process of preparing astragalus polysaccharides, comprising:

putting astragalus after being pulverized and being degreased by ethanol into a microwave extraction chamber, adding 10%-35% oxalic acid of 1.5 to 2.5 times of the weight thereof, at a microwave power density 1-2 KW/Kg under 500 mmHg-760 mmHg pressure maintaining the reflux of oxalic acid solution for 15-30 min, and then evaporating under reduced pressure the liquid in the microwave extraction chamber to dryness. An ethanol solution of 3-5 times of the weight of the astragalus is added to the reaction chamber. The mixer is stirred and washed for 40-60 minutes and filtered. The filtration residue after drying is extracted twice with water, wherein each time the amount of water is 6-8 times of the weight of the residue, the extraction temperature is 70° C., and the extraction time is about 40 minutes. Filtration is conducted and the two filtrate solutions are combined, and concentrated to a volume of ⅕ of the original extracting solution; then ethanol is added for precipitation, and the precipitates are dried to obtain astragalus polysaccharides.

The present invention also provides astragalus polysaccharides prepared using the above process, wherein the molecular weight distribution of said astragalus polysaccharides is 3000-40000.

In the process of the present invention, as one of the embodiments, the present invention further provides a process of preparing wolfberry polysaccharides, comprising:

putting wolfberry after being degreased by petroleum ether or ethanol into a microwave extraction chamber, adding 30%-85% formic acid solution of 1 to 2.5 times of the weight thereof, at a microwave power density 1-2 KW/Kg under 500 mmHg-760 mmHg pressure maintaining the reflux of formic acid solution for 15-25 min, and then evaporating under reduced pressure the formic acid to dryness. An ethanol solution of 3-5 times of the weight of the wolfberry is added to the reaction chamber. The mixer is stirred and washed for 40-60 minutes and filtered. The filtration residue after drying is extracted twice with water, wherein each time the amount of water is 6-8 times of the weight of the residue, the extraction temperature is 70° C., and the extraction time is about 40 minutes. Filtration is conducted and the two filtrate solutions are combined, and concentrated to a volume of ⅕ of the original extracting solution; then ethanol is added for precipitation, and the precipitates are dried to obtain wolfberry polysaccharides.

The present invention also provides wolfberry polysaccharides prepared using the above process, wherein the molecular weight distribution of said wolfberry polysaccharides is 3000-20000.

In the process of the present invention, as one of the embodiments, the present invention further provides a process of preparing yam polysaccharides, comprising:

putting yam after being pulverized into a microwave extraction chamber, adding 70%-95% propionic acid solution of 1.5 to 2.5 times of the weight thereof, at a microwave power density 1-2 KW/Kg under 500 mmHg-760 mmHg pressure maintaining the reflux of propionic acid solution for 15-25 min, and then evaporating under reduced pressure the propionic acid to dryness. An ethanol solution of 3-5 times of the weight of the yam is added to the reaction chamber. The mixer is stirred and washed for 40-60 minutes and filtered. The filtration residue after drying is extracted twice with water, wherein each time the amount of water is 6-8 times of the weight of the residue, the extraction temperature is 70° C., and the extraction time is about 40 minutes. Filtration is conducted and the two filtrate solutions are combined, and concentrated to a volume of ⅕ of the original extracting solution; then ethanol is added for precipitation, and the precipitates are dried to obtain yam polysaccharides.

The present invention also provides yam polysaccharides prepared using the above process, wherein the molecular weight distribution of said yam polysaccharides is 3000-20000.

In the process of the present invention, as one of the embodiments, the present invention further provides a process of preparing gingko polysaccharides, comprising:

putting gingko after being pulverized and being degreased by ethanol into a microwave extraction chamber, adding 30%-85% formic acid solution of 1.5 to 2.5 times of the weight thereof, at a microwave power density 1-2 KW/Kg under 500 mmHg-760 mmHg pressure maintaining the reflux of formic acid solution for 15-25 min, and then evaporating under reduced pressure the formic acid to dryness. An ethanol solution of 4-6 times of the weight of the gingko is added to the reaction chamber. The mixer is stirred and washed for 40-60 minutes and filtered. The filtration residue after drying is extracted twice with water, wherein each time the amount of water is 6-8 times of the weight of the residue, the extraction temperature is 70° C., and the extraction time is about 40 minutes. Filtration is conducted and the two filtrate solutions are combined, and concentrated to a volume of ⅕ of the original extracting solution; then ethanol is added for precipitation, and the precipitates are dried to obtain gingko polysaccharides.

The present invention also provides gingko polysaccharides prepared using the above process, wherein the molecular weight distribution of said gingko polysaccharides is 5000-12000.

In the process of the present invention, as one of the embodiments, the present invention further provides a process of preparing panax pseudoginseng polysaccharides, comprising:

putting panax pseudoginseng after being pulverized and being degreased by ethanol into a microwave extraction chamber, adding 60%-95% acetic acid solution of 1.5 to 2.5 times of the weight thereof, at a microwave power density 1-2 KW/Kg under 500 mmHg-760 mmHg pressure maintaining the reflux of acetic acid solution for 15-25 min, and then evaporating under reduced pressure the acetic acid to dryness. An ethanol solution of 3-5 times of the weight of the panax pseudoginseng is added to the reaction chamber. The mixer is stirred and washed for 40-60 minutes and filtered. The filtration residue after drying is extracted twice with water, wherein each time the amount of water is 6-8 times of the weight of the residue, the extraction temperature is 70° C., and the extraction time is about 40 minutes. Filtration is conducted and the two filtrate solutions are combined, and concentrated to a volume of ⅕ of the original extracting solution; then ethanol is added for precipitation, and the precipitates are dried to obtain panax pseudoginseng polysaccharides.

The present invention also provides panax pseudoginseng polysaccharides prepared using the above process, wherein the molecular weight distribution of said panax pseudoginseng polysaccharides is 4000-20000.

In the process of the present invention, as one of the embodiments, the present invention further provides a process of preparing plantago polysaccharides, comprising:

putting plantago after being degreased by petroleum ether and ethanol into a microwave extraction chamber, adding 80%-95% propionic acid solution of 1.5 to 2.5 times of the weight thereof, at a microwave power density 1-2 KW/Kg under 500 mmHg-760 mmHg pressure maintaining the reflux of propionic acid solution for 15-25 min, and then evaporating under reduced pressure the propionic acid to dryness. An ethanol solution of 3-5 times of the weight of the plantago is added to the reaction chamber. The mixer is stirred and washed for 40-60 minutes and filtered. The filtration residue after drying is extracted twice with water, wherein each time the amount of water is 6-8 times of the weight of the residue, the extraction temperature is 70° C., and the extraction time is about 40 minutes. Filtration is conducted and the two filtrate solutions are combined, and concentrated to a volume of ⅕ of the original extracting solution; then ethanol is added for precipitation, and the precipitates are dried to obtain plantago polysaccharides.

The present invention also provides plantago polysaccharides prepared using the above process, wherein the molecular weight distribution of said plantago polysaccharides is 4000-30000.

In the process of the present invention, as one of the embodiments, the present invention further provides a process of preparing gastrodia elata polysaccharides, comprising:

putting gastrodia elata after being pulverized and being degreased by ethanol into a microwave extraction chamber, adding a formic acid-hydrochloride acid mixed solution (0.3%-0.6% hydrochloride acid and 30%-85% formic acid)

of 1.5 to 2.5 times of the weight thereof, at a microwave power density 1-2 KW/Kg under 500 mmHg-760 mmHg pressure maintaining the reflux of the acids mixed solution for 15-25 min, and then evaporating under reduced pressure the acids mixed solution to dryness. An ethanol solution of 3-5 times of the weight of the gastrodia data is added to the reaction chamber. The mixer is stirred and washed for 40-60 minutes and filtered. The filtration residue after drying is extracted twice with water, wherein each time the amount of water is 6-8 times of the weight of the residue, the extraction temperature is 70° C., and the extraction time is about 40 minutes. Filtration is conducted and the two filtrate solutions are combined, and concentrated to a volume of ⅕ of the original extracting solution; then ethanol is added for precipitation, and the precipitates are dried to obtain gastrodia elata polysaccharides.

The present invention also provides gastrodia elata polysaccharides prepared using the above process, wherein the molecular weight distribution of said gastrodia elata polysaccharides is 3000-20000.

In the process of the present invention, as one of the embodiments, the present invention further provides a process of preparing eucommia ulmoides polysaccharides, comprising:

putting eucommia ulmoides after being pulverized and being degreased by ethanol into a microwave extraction chamber, adding 30%-85% formic acid solution of 1.5 to 2.5 times of the weight thereof, at a microwave power density 1-2 KW/Kg under 500 mmHg-760 mmHg pressure maintaining the reflux of formic acid solution for 15-25 min, and then evaporating under reduced pressure the formic acid to dryness. An ethanol solution of 3-5 times of the weight of the eucommia ulmoides is added to the reaction chamber. The mixer is stirred and washed for 40-60 minutes and filtered. The filtration residue after drying is extracted twice with water, wherein each time the amount of water is 6-8 times of the weight of the residue, the extraction temperature is 70° C., and the extraction time is about 40 minutes. Filtration is conducted and the two filtrate solutions are combined, and concentrated to a volume of ⅕ of the original extracting solution; then ethanol is added for precipitation, and the precipitates are dried to obtain eucommia ulmoides polysaccharides.

The present invention also provides eucommia ulmoides polysaccharides prepared using the above process, wherein the molecular weight distribution of said eucommia ulmoides polysaccharides is 3000-20000.

In the process of the present invention, as one of the embodiments, the present invention further provides a process of preparing salvia polysaccharides, comprising:

putting salvia after being pulverized and being degreased by ethanol into a microwave extraction chamber, adding 60%-95% acetic acid solution of 1.5 to 2.5 times of the weight thereof, at a microwave power density 1-2 KW/Kg under 500 mmHg-760 mmHg pressure maintaining the reflux of acetic acid solution for 15-25 min, and then evaporating under reduced pressure the acetic acid to dryness. An ethanol solution of 3-5 times of the weight of the salvia is added to the reaction chamber. The mixer is stirred and washed for 40-60 minutes and filtered. The filtration residue after drying is extracted twice with water, wherein each time the amount of water is 6-8 times of the weight of the residue, the extraction temperature is 70° C., and the extraction time is about 40 minutes. Filtration is conducted and the two filtrate solutions are combined, and concentrated to a volume of ⅕ of the original extracting solution; then ethanol is added for precipitation, and the precipitates are dried to obtain salvia polysaccharides.

The present invention also provides salvia polysaccharides prepared using the above process, wherein the molecular weight distribution of said salvia polysaccharides is 5000-25000.

In the process of the present invention, as one of the embodiments, the present invention further provides a process of preparing kudzu polysaccharides, comprising:

putting kudzu after being pulverized and being degreased by ethanol into a microwave extraction chamber, adding 70%-95% propionic acid solution of 1.5 to 2.5 times of the weight thereof, at a microwave power density 1-2 KW/Kg under 500 mmHg-760 mmHg pressure maintaining the reflux of propionic acid solution for 15-25 min, and then evaporating under reduced pressure the propionic acid to dryness. An ethanol solution of 3-5 times of the weight of the kudzu is added to the reaction chamber. The mixer is stirred and washed for 40-60 minutes and filtered. The filtration residue after drying is extracted twice with water, wherein each time the amount of water is 6-8 times of the weight of the residue, the extraction temperature is 70° C., and the extraction time is about 40 minutes. Filtration is conducted and the two filtrate solutions are combined, and concentrated to a volume of ⅕ of the original extracting solution; then ethanol is added for precipitation, and the precipitates are dried to obtain kudzu polysaccharides.

The present invention also provides kudzu polysaccharides prepared using the above process, wherein the molecular weight distribution of said kudzu polysaccharides is 3000-25000.

In the process of the present invention, as one of the embodiments, the present invention further provides a process of preparing lucid ganoderma polysaccharides, comprising:

putting lucid ganoderma sporocarp after being pulverized and being degreased by ethanol into a microwave extraction chamber, adding 10%-35% oxalic acid solution of 1.5 to 2.5 times of the weight thereof, at a microwave power density 1-2 KW/Kg under 500 mmHg-760 mmHg pressure maintaining the reflux of oxalic acid solution for 15-25 min, and then evaporating under reduced pressure the liquid to dryness. An ethanol solution of 3-5 times of the weight of the lucid ganoderma sporocarp is added to the reaction chamber. The mixer is stirred and washed for 40-60 minutes and filtered. The filtration residue after drying is extracted twice with water, wherein each time the amount of water is 6-8 times of the weight of the residue, the extraction temperature is 70° C., and the extraction time is about 40 minutes. Filtration is conducted and the two filtrate solutions are combined, and concentrated to a volume of ⅕ of the original extracting solution; then ethanol is added for precipitation, and the precipitates are dried to obtain lucid ganoderma polysaccharides.

The present invention also provides lucid ganoderma polysaccharides prepared using the above process, wherein the molecular weight distribution of said lucid ganoderma polysaccharides is 3000-12000.

In the process of the present invention, as one of the embodiments, the present invention further provides a process of preparing poria polysaccharides, comprising:

putting poria after being pulverized and being degreased by ethanol into a microwave extraction chamber, adding 30%-85% formic acid solution of 1.5 to 2.5 times of the weight thereof, at a microwave power density 1-2 KW/Kg under 500 mmHg-760 mmHg pressure maintaining the reflux of formic acid solution for 15-25 min, and then evaporating under reduced pressure the formic acid to dryness. An ethanol solution of 3-5 times of the weight of the poria is added to the reaction chamber. The mixer is stirred and washed for 40-60 minutes and filtered. The filtration residue after drying is extracted twice with water, wherein each time the amount of water is 6-8 times of the weight of the residue, the extraction temperature is 70° C., and the extraction time is about 40 minutes. Filtration is conducted and the two filtrate solutions are combined, and concentrated to a volume of ⅕ of the original extracting solution; then ethanol is added for precipitation, and the precipitates are dried to obtain poria polysaccharides.

The present invention also provides poria polysaccharides prepared using the above process, wherein the molecular weight distribution of said poria polysaccharides is 2000-8000.

In the process of the present invention, as one of the embodiments, the present invention further provides a process of preparing exidia auricula judae polysaccharides, comprising:

putting exidia auricula judae after being pulverized into a microwave extraction chamber, adding 60%-95% acetic acid solution of 1.5 to 2.5 times of the weight thereof, at a microwave power density 1-2 KW/Kg under 500 mmHg-760 mmHg pressure maintaining the reflux of acetic acid solution for 15-25 min, and then evaporating under reduced pressure the acetic acid to dryness. An ethanol solution of 3-5 times of the weight of the exidia auricula judae is added to the reaction chamber. The mixer is stirred and washed for 40-60 minutes and filtered. The filtration residue after drying is extracted twice with water, wherein each time the amount of water is 6-8 times of the weight of the residue, the extraction temperature is 70° C., and the extraction time is about 40 minutes. Filtration is conducted and the two filtrate solutions are combined, and concentrated to a volume of ⅕ of the original extracting solution; then ethanol is added for precipitation, and the precipitates are dried to obtain exidia auricula judae polysaccharides.

The present invention also provides exidia auricula judae polysaccharides prepared using the above process, wherein the molecular weight distribution of said exidia auricula judae polysaccharides is 5000-40000.

In the process of the present invention, as one of the embodiments, the present invention further provides a process of preparing mushroom polysaccharides, comprising:

putting mushroom sporocarp after being pulverized into a microwave extraction chamber, adding 70%-95% propionic acid solution of 1.5 to 2.5 times of the weight thereof, at a microwave power density 1-2 KW/Kg under 500 mmHg-760 mmHg pressure maintaining the reflux of propionic acid solution for 15-25 min, and then evaporating under reduced pressure the propionic acid to dryness. An ethanol solution of 3-5 times of the weight of the mushroom is added to the reaction chamber. The mixer is stirred and washed for 40-60 minutes and filtered. The filtration residue after drying is extracted twice with water, wherein each time the amount of water is 6-8 times of the weight of the residue, the extraction temperature is 70° C., and the extraction time is about 40 minutes. Filtration is conducted and the two filtrate solutions are combined, and concentrated to a volume of ⅕ of the original extracting solution; then ethanol is added for precipitation, and the precipitates are dried to obtain mushroom polysaccharides.

The present invention also provides mushroom polysaccharides prepared using the above process, wherein the molecular weight distribution of said mushroom polysaccharides is 3000-15000.

The present invention has the following features:

First, using a microwave with an organic acid or a mixed acids containing an organic acid directly works on medicinal raw materials, utilizing the organic acid cleaves bonds between polysaccharides and macromolecules (including chitin, cellulose and proteins) of cell walls of plants and fungi, as to promote the release of polysaccharides from said medicinal materials and improve the extraction yield of polysaccharides; besides regarding the organic acid, in addition to $H^+$ ions's degradation effects on polysaccharides, organic acid radical ions can protect polysaccharide molecules by forming hydrogen bonds with hydroxyl groups of the polysaccharides.

Second, the organic acid or the mixed acids containing an organic acid enhanced by microwave can further moderately degrade released polysaccharides, thereby significantly enhancing the water-solubility of the polysaccharides. Polysaccharides with relatively centralized molecular weight distribution and good water-solubility are obtained and the whole process achieves the efficient extraction and restructuring of higher plants and fungi polysaccharides.

Third, microwave heating can ensure inside and outside of the materials are simultaneously heated and sufficiently overcome a series of insurmountable issues like uneven heating of materials and high energy consumption in conventional heating methods.

Compared with prior art, the present invention further has the following advantages:

1. The present invention saves time, uses less organic acids or a mixed acids containing an organic acid and has easy and efficient recycling and remarkable water and energy saving effects. Using microwave heating technology effectively overcomes the heat transmission problem which is difficult to avoid in conventional heating methods, significantly reducing the amount of organic acids used and processing time, especially in the distillation process of removing acids, can overcome the uneven heating problem which is insurmountable in conventional heating methods. This feature in the large-scale production has been particularly remarkable.

2. The organic acid or the mixed acids containing an organic acid enhanced by microwave can further moderately adjust the molecular structure of released higher plants and fungi polysaccharides, as to significantly improve the water solubility of polysaccharides; while regarding the organic acid, in addition to $H^+$ ions's degradation effects on polysaccharides, organic acid radical ions can protect polysaccharide molecules by forming hydrogen bonds with hydroxyl groups of the polysaccharides.

The process of the present invention uses an organic acid or a mixed acids containing an organic acid to directly work on medicinal raw materials, overcomes many disadvantages of polysaccharides extraction in prior art. The active polysaccharides obtained through the process of the present invention has better biological activities.

BRIEF DESCRIPTION OF THE DRAWINGS

FIG. 1 is a process flow diagram of the present invention.

EMBODIMENTS

The present invention will be further illustrated by the following Examples and Experimental Examples.

The process of the present invention is as follows:

1) putting pretreated higher plants, fungi raw materials into a microwave reactor chamber, adding an organic acid or an organic/inorganic acid mixed solution therein to, sufficiently stirring to make the powder be well wetted;

2) microwave treatment, applying microwave power, using cooperative effects among microwave, organic acid molecules and organic macromolecular substances of cell wall of higher plants, fungi to separate polysaccharides from flowers, leaves, fruits, or rhizomes of said higher plants, or mycelium or sporocarp of fungi, and selectively cutting the glycosidic bonds of the macromolecular polysaccharides, as to achieve moderate degradation thereof;

3) using distillation under reduced pressure by microwave heating to remove most of the organic acids or the organic/inorganic acid mixed solution, and sufficiently washing with an organic solvent to remove a small amount of residual acid in the materials to complete the microwave pretreatment of higher plants, fungi raw materials;

4) adding about 5-15 times of water to extract microwave pretreated higher plants or fungi, wherein the extracting solution after concentration is subjected to alcohol precipitation to obtain excellent water-soluble crude polysaccharides.

The whole process is shown in FIG. 1.

In the examples, the extraction yield, the polysaccharide content, the polysaccharide molecular weight distribution, the amount of organic acids, reaction time and other data are shown in Table 1. Wherein, polysaccharide extraction yield is the weight percentage of products to higher plant raw materials, the polysaccharide content is measured by sulfuric acid-phenol method reported in an agricultural and technology magazine (Shiling Sun, Method for Determination of polysaccharide content of yam, "Agriculture and Technology", 2010, 20 (3), 35-39), polysaccharide molecular weight distribution is determined by gel chromatography (composition analysis of astragalus polysaccharide, Yaping Cai, Rui Zhao, Dan Zhu, "China Journal of Experimental Traditional Medical Formulae", 2011, 17 (1), 81-83.)

Example 1

1) 1.5 kg dry, clean and mechanically pulverized astragalus is put in an extraction container, 10 L ethanol is added, the mixer is heated until reflux to extract for 1 h, and the above procedure is repeated once;
2) Filtration is conducted, the two filtrates are combined and distilled under reduced pressure to recover ethanol, as to obtain a alcohol extract rich in liposoluble active components including flavonoids, saponins, and coumarin, etc., and the filtration residue is dried at 60-80° C. for further process;
3) The dry filtration residue in the step 2) is placed in a travelling wave microwave reaction chamber;
4) 300 g oxalic acid is added with water to prepare 10% oxalic acid solution;
5) 3 L oxalic acid solution of the step 4) is added into above mentioned microwave reaction chamber, and the mixer is sufficiently stirred to evenly wet the material;
6) Above mentioned mixer is subjected to irradiation at 5 KW continuous microwave power until the liquid refluxes, i.e., the organic acid solution is vaporized, and then the microwave is switched to a pulsed microwave power operating mode, wherein the duty ratio is 5 seconds/5 seconds (i.e. the ratio of on-time and off-time), peak power is 10 KW; after 15 min, vacuuming is conducted (reaction chamber working pressure is 20 mmHg) until no liquid is in the microwave reaction chamber;
7) 5 L absolute ethanol is added into astragalus treated by microwave in the step 6), sufficiently stirred, and filtered, wherein the filtrate is distilled to recover ethanol and oxalic acid, and the filtration residue after being dried is microwave treated astragalus;
8) 100 g microwave treated astragalus of the step 7) is placed in a 1 L beaker, 500 ml distill water is added thereinto, and the mixer is placed in a hot water bath at 70° C. for 40 min for extraction and then filtered. The above procedure is repeated once. The two filtrates are combined;
9) The filtrate after being concentrated is subjected to alcohol precipitation, and the precipitate is dried to obtain active polysaccharides;
10) Data including polysaccharide extraction yield, polysaccharide content, polysaccharide molecular weight distribution and amount of water used for extraction are listed in Table 1.

Example 2

1) 1.5 kg dry wolfberry is put in an extraction container, 10 L petroleum ether is added, the mixer is heated until reflux to extract for 1 h and filtered; the filtration residue is added with 10 L ethanol, and heated until reflux to extract for 1 h;
2) Filtration is conducted, the filtrate is distilled under reduced pressure to recover ethanol, as to obtain a alcohol extract rich in liposoluble active components including wolfberry color, and the filtration residue is dried at 60-80° C. for further process;
3) The dry filtration residue in the step 2) is placed in a travelling wave microwave reaction chamber;
4) 2.4 L pure formic acid is added with water to prepare 70% formic acid solution;
5) 3 L formic acid solution of the step 4) is added into above mentioned microwave reaction chamber, and the mixer is sufficiently stirred to evenly wet the material;
6) Above mentioned mixer is subjected to irradiation at 6 KW continuous microwave power until the liquid refluxes, i.e., the organic acid solution is vaporized, and then the microwave is switched to a pulsed microwave power operating mode, wherein the duty ratio is 5 seconds/5 seconds (i.e. the ratio of on-time and off-time), peak power is 8 KW; after 25 min, vacuuming is conducted (reaction chamber working pressure is 20 mmHg) until no liquid is in the microwave reaction chamber;
7) 5 L absolute ethanol is added into wolfberry treated by microwave in the step 6), sufficiently stirred, and filtered, wherein the filtrate is distilled to recover ethanol, and the filtration residue after being dried is microwave treated wolfberry;
8) 100 g microwave treated wolfberry of the step 7) is placed in a 1 L beaker, 500 ml distill water is added thereinto, and the mixer is placed in a hot water bath at 70° C. for 40 min for extraction and then filtered. The above procedure is repeated once. The two filtrates are combined;
9) The filtrate after being concentrated is subjected to alcohol precipitation, and the precipitate is dried to obtain active polysaccharides;

10) Data including polysaccharide extraction yield, polysaccharide content, polysaccharide molecular weight distribution and amount of water used for extraction are listed in Table 1, Example 3

1) 1.5 kg dry, clean and mechanically pulverized yam is put in a travelling wave microwave reaction chamber;
2) 2.8 L pure propionic acid is added with water to prepare 90% propionic acid solution;
3) 3 L propionic acid solution of the step 2) is added into above mentioned microwave reaction chamber, and the mixer is sufficiently stirred to evenly wet the material;
4) Above mentioned mixer is subjected to irradiation at 5 KW continuous microwave power until the liquid refluxes, i.e., the organic acid solution is vaporized, and then the microwave is switched to a pulsed microwave power operating mode, wherein the duty ratio is 5 seconds/5 seconds (i.e. the ratio of on-time and off-time), peak power is 8 KW; after 20 min, vacuuming is conducted (reaction chamber working pressure is 20 mmHg) until no liquid is in the microwave reaction chamber;
5) 5 L absolute ethanol is added into the yam treated by microwave in the step 4), sufficiently stirred, and filtered, wherein the filtrate is distilled to recover ethanol, and the filtration residue after being dried is microwave treated yam;
6) 100 g microwave treated yam of the step 7) is placed in a 1 L beaker, 800 ml distill water is added thereinto, and the mixer is placed in a hot water bath at 70° C. for 40 min for extraction and then filtered. The above procedure is repeated once. The two filtrates are combined;
7) The filtrate after being concentrated is subjected to alcohol precipitation, and the precipitate is dried to obtain active polysaccharides;
8) Data including polysaccharide extraction yield, polysaccharide content, polysaccharide molecular weight distribution and amount of water used for extraction are listed in Table 1.

Example 4

1) 1.5 kg dry, clean and mechanically pulverized gingko is put in an extraction container, 10 L ethanol is added, the mixer is heated until reflux to extract for 1 h, and the above procedure is repeated once;
2) Filtration is conducted, the filtrate is distilled under reduced pressure to recover ethanol, as to obtain a alcohol extract rich in liposoluble active components including flavone and lactone, and the filtration residue is dried at 60-80° C. for further process;
3) The dry filtration residue in the step 2) is placed in a travelling wave microwave reaction chamber;
4) 2.8 L pure formic acid is added with water to prepare 30% formic acid solution;
5) 3 L formic acid solution of the step 4) is added into above mentioned microwave reaction chamber, and the mixer is sufficiently stirred to evenly wet the material;
6) Above mentioned mixer is subjected to irradiation at 4 KW continuous microwave power until the liquid refluxes, i.e., the organic acid solution is vaporized, and then the microwave is switched to a pulsed microwave power operating mode, wherein the duty ratio is 5 seconds/5 seconds (i.e. the ratio of on-time and off-time), peak power is 6 KW; after 15 min, vacuuming is conducted (reaction chamber working pressure is 20 mmHg) until no liquid is in the microwave reaction chamber;
7) 5 L absolute ethanol is added into gingko treated by microwave in the step 6), sufficiently stirred, and filtered, wherein the filtrate is distilled to recover ethanol, and the filtration residue after being dried is microwave treated gingko;
8) 100 g microwave treated gingko of the step 7) is placed in a 1 L beaker, 600 ml distill water is added thereinto, and the mixer is placed in a hot water bath at 70° C. for 40 min for extraction and then filtered. The above procedure is repeated once. The two filtrates are combined;
9) The filtrate after being concentrated is subjected to alcohol precipitation, and the precipitate is dried to obtain active polysaccharides;
10) Data including polysaccharide extraction yield, polysaccharide content, polysaccharide molecular weight distribution and amount of water used for extraction are listed in Table 1.

Example 5

1) 1.5 kg dry, clean and mechanically pulverized panax pseudoginseng is put in an extraction container, 10 L ethanol is added, the mixer is heated until reflux to extract for 1 h, and the above procedure is repeated once;
2) Filtration is conducted, the filtrate is distilled under reduced pressure to recover ethanol, as to obtain a alcohol extract rich in liposoluble active components including triterpenoid saponin, and the filtration residue is dried at 60-80° C. for further process;
3) The dry filtration residue in the step 2) is placed in a travelling wave microwave reaction chamber;
4) 2.8 L pure acetic acid is added with water to prepare 85% acetic acid solution;
5) 3 L acetic acid solution of the step 4) is added into above mentioned microwave reaction chamber, and the mixer is sufficiently stirred to evenly wet the material;
6) Above mentioned mixer is subjected to irradiation at 6 KW continuous microwave power until the liquid refluxes, i.e., the organic acid solution is vaporized, and then the microwave is switched to a pulsed microwave power operating mode, wherein the duty ratio is 5 seconds/5 seconds (i.e. the ratio of on-time and off-time), peak power is 8 KW; after 15 min, vacuuming is conducted (reaction chamber working pressure is 20 mmHg) until no liquid is in the microwave reaction chamber;
7) 5 L absolute ethanol is added into panax pseudoginseng treated by microwave in the step 6), sufficiently stirred, and filtered, wherein the filtrate is distilled to recover ethanol, and the filtration residue after being dried is microwave treated panax pseudoginseng;
8) 100 g microwave treated panax pseudoginseng of the step 7) is placed in a 1 L beaker, 500 ml distill water is added thereinto, and the mixer is placed in a hot water bath at 70° C. for 40 min for extraction and then filtered. The above procedure is repeated once. The two filtrates are combined;
9) The filtrate after being concentrated is subjected to alcohol precipitation, and the precipitate is dried to obtain active polysaccharides;

10) Data including polysaccharide extraction yield, polysaccharide content, polysaccharide molecular weight distribution and amount of water used for extraction are listed in Table 1.

Example 6

1) 1.5 kg dry plantago is put in an extraction container, 10 L petroleum ether is added, the mixer is heated until reflux to extract for 1 h and filtered; the filtration residue is added with 10 L ethanol, and heated until reflux to extract for 1 h;
2) Filtration is conducted, the filtrate is distilled under reduced pressure to recover ethanol, as to obtain a alcohol extract rich in liposoluble active components including fatty acid, and the filtration residue is dried at 60-80° C. for further process;
3) The dry filtration residue in the step 2) is placed in a travelling wave microwave reaction chamber;
4) 3 L pure propionic acid is added with water to prepare 90% propionic acid solution;
5) 3 L propionic acid solution of the step 4) is added into above mentioned microwave reaction chamber, and the mixer is sufficiently stirred to evenly wet the material;
6) Above mentioned mixer is subjected to irradiation at 5 KW continuous microwave power until the liquid refluxes, i.e., the organic acid solution is vaporized, and then the microwave is switched to a pulsed microwave power operating mode, wherein the duty ratio is 5 seconds/5 seconds (i.e. the ratio of on-time and off-time), peak power is 10 KW; after 20 min, vacuuming is conducted (reaction chamber working pressure is 20 mmHg) until no liquid is in the microwave reaction chamber;
7) 5 L absolute ethanol is added into plantago treated by microwave in the step 6), sufficiently stirred, and filtered, wherein the filtrate is distilled to recover ethanol, and the filtration residue after being dried is microwave treated plantago;
8) 100 g microwave treated plantago of the step 7) is placed in a 1 L beaker, 500 ml distill water is added thereinto, and the mixer is placed in a hot water bath at 70° C. for 40 min for extraction and then filtered. The above procedure is repeated once. The two filtrates are combined;
9) The filtrate after being concentrated is subjected to alcohol precipitation, and the precipitate is dried to obtain active polysaccharides;
10) Data including polysaccharide extraction yield, polysaccharide content, polysaccharide molecular weight distribution and amount of water used for extraction are listed in Table 1.

Example 7

1) 1.5 kg dry, clean and mechanically pulverized gastrodia elata is put in an extraction container, 10 L ethanol is added, the mixer is heated until reflux to extract for 1 h, and the above procedure is repeated once;
2) Filtration is conducted, the filtrate is distilled under reduced pressure to recover ethanol, as to obtain a alcohol extract rich in liposoluble active components including phenolic acids, and the filtration residue is dried at 60-80° C. for further process;
3) The dry filtration residue in the step 2) is placed in a travelling wave microwave reaction chamber;
4) 2.8 L pure formic acid is added with 100 ml 36% concentrated hydrochloride acid and water to prepare a formic acid-hydrochloride acid mixed solution (0.5% hydrochloride acid and 75% formic acid);
5) 3 L formic acid-hydrochloride acid mixed solution of the step 4) is added into above mentioned microwave reaction chamber, and the mixer is sufficiently stirred to evenly wet the material;
6) Above mentioned mixer is subjected to irradiation at 6 KW continuous microwave power until the liquid refluxes, i.e., the organic acid solution is vaporized, and then the microwave is switched to a pulsed microwave power operating mode, wherein the duty ratio is 5 seconds/5 seconds (i.e. the ratio of on-time and off-time), peak power is 8 KW; after 15 min, vacuuming is conducted (reaction chamber working pressure is 20 mmHg) until no liquid is in the microwave reaction chamber;
7) 5 L absolute ethanol is added into gastrodia data treated by microwave in the step 6), sufficiently stirred, and filtered, wherein the filtrate is distilled to recover ethanol, and the filtration residue after being dried is microwave treated gastrodia data;
8) 100 g microwave treated gastrodia data of the step 7) is placed in a 1 L beaker, 800 ml distill water is added thereinto, and the mixer is placed in a hot water bath at 70° C. for 40 min for extraction and then filtered. The above procedure is repeated once. The two filtrates are combined;
9) The filtrate after being concentrated is subjected to alcohol precipitation, and the precipitate is dried to obtain active polysaccharides;
10) Data including polysaccharide extraction yield, polysaccharide content, polysaccharide molecular weight distribution and amount of water used for extraction are listed in Table 1.

Example 8

1) 1.5 kg dry, clean and mechanically pulverized eucommia ulmoides is put in an extraction container, 10 L ethanol is added, the mixer is heated until reflux to extract for 1 h, and the above procedure is repeated once;
2) Filtration is conducted, the filtrate is distilled under reduced pressure to recover ethanol, as to obtain a alcohol extract rich in liposoluble active components including lignans, and the filtration residue is dried at 60-80° C. for further process;
3) The dry filtration residue in the step 2) is placed in a travelling wave microwave reaction chamber;
4) 2.8 L pure formic acid is added with water to prepare 80% formic acid solution;
5) 3 L formic acid solution of the step 4) is added into above mentioned microwave reaction chamber, and the mixer is sufficiently stirred to evenly wet the material;
6) Above mentioned mixer is subjected to irradiation at 6 KW continuous microwave power until the liquid refluxes, i.e., the organic acid solution is vaporized, and then the microwave is switched to a pulsed microwave power operating mode, wherein the duty ratio is 5 seconds/5 seconds (i.e. the ratio of on-time and off-time), peak power is 8 KW; after 15 min, vacuuming is conducted (reaction chamber working pressure is 20 mmHg) until no liquid is in the microwave reaction chamber;

7) 5 L absolute ethanol is added into eucommia ulmoides treated by microwave in the step 6), sufficiently stirred, and filtered, wherein the filtrate is distilled to recover ethanol, and the filtration residue after being dried is microwave treated eucommia ulmoides;
8) 100 g microwave treated eucommia ulmoides of the step 7) is placed in a 1 L beaker, 800 ml distill water is added thereinto, and the mixer is placed in a hot water bath at 70° C. for 40 min for extraction and then filtered. The above procedure is repeated once. The two filtrates are combined;
9) The filtrate after being concentrated is subjected to alcohol precipitation, and the precipitate is dried to obtain active polysaccharides;
10) Data including polysaccharide extraction yield, polysaccharide content, polysaccharide molecular weight distribution and amount of water used for extraction are listed in Table 1.

Example 9

1) 1.5 kg dry, clean and mechanically pulverized salvia is put in an extraction container, 10 L ethanol is added, the mixer is heated until reflux to extract for 1 h, and the above procedure is repeated once;
2) Filtration is conducted, the filtrate is distilled under reduced pressure to recover ethanol, as to obtain a alcohol extract rich in liposoluble active components including salvianolic acid, and the filtration residue is dried at 60-80° C. for further process;
3) The dry filtration residue in the step 2) is placed in a travelling wave microwave reaction chamber;
4) 2.8 L pure acetic acid is added with water to prepare 85% acetic acid solution;
5) 3 L acetic acid solution of the step 4) is added into above mentioned microwave reaction chamber, and the mixer is sufficiently stirred to evenly wet the material;
6) Above mentioned mixer is subjected to irradiation at 5 KW continuous microwave power until the liquid refluxes, i.e., the organic acid solution is vaporized, and then the microwave is switched to a pulsed microwave power operating mode, wherein the duty ratio is 5 seconds/5 seconds (i.e. the ratio of on-time and off-time), peak power is 10 KW; after 20 min, vacuuming is conducted (reaction chamber working pressure is 20 mmHg) until no liquid is in the microwave reaction chamber;
7) 5 L absolute ethanol is added into salvia treated by microwave in the step 6), sufficiently stirred, and filtered, wherein the filtrate is distilled to recover ethanol, and the filtration residue after being dried is microwave treated salvia;
8) 100 g microwave treated salvia of the step 7) is placed in a 1 L beaker, 600 ml distill water is added thereinto, and the mixer is placed in a hot water bath at 70° C. for 40 min for extraction and then filtered. The above procedure is repeated once. The two filtrates are combined;
9) The filtrate after being concentrated is subjected to alcohol precipitation, and the precipitate is dried to obtain active polysaccharides;
10) Data including polysaccharide extraction yield, polysaccharide content, polysaccharide molecular weight distribution and amount of water used for extraction are listed in Table 1.

Example 10

1) 1.5 kg dry, clean and mechanically pulverized kudzu is put in an extraction container, 10 L ethanol is added, the mixer is heated until reflux to extract for 1 h, and the above procedure is repeated once;
2) Filtration is conducted, the filtrate is distilled under reduced pressure to recover ethanol, as to obtain a alcohol extract rich in liposoluble active components including flavonoids and saponins, and the filtration residue is dried at 60-80° C. for further process;
3) The dry filtration residue in the step 2) is placed in a travelling wave microwave reaction chamber;
4) 3.0 L pure propionic acid is added with water to prepare 90% propionic acid solution;
5) 3 L propionic acid solution of the step 4) is added into above mentioned microwave reaction chamber, and the mixer is sufficiently stirred to evenly wet the material;
6) Above mentioned mixer is subjected to irradiation at 5 KW continuous microwave power until the liquid refluxes, i.e., the organic acid solution is vaporized, and then the microwave is switched to a pulsed microwave power operating mode, wherein the duty ratio is 5 seconds/5 seconds (i.e. the ratio of on-time and off-time), peak power is 8 KW; after 25 min, vacuuming is conducted (reaction chamber working pressure is 20 mmHg) until no liquid is in the microwave reaction chamber;
7) 5 L absolute ethanol is added into kudzu treated by microwave in the step 6), sufficiently stirred, and filtered, wherein the filtrate is distilled to recover ethanol, and the filtration residue after being dried is microwave treated kudzu;
8) 100 g microwave treated kudzu of the step 7) is placed in a 1 L beaker, 800 ml distill water is added thereinto, and the mixer is placed in a hot water bath at 70° C. for 40 min for extraction and then filtered. The above procedure is repeated once. The two filtrates are combined;
9) The filtrate after being concentrated is subjected to alcohol precipitation, and the precipitate is dried to obtain active polysaccharides;
10) Data including polysaccharide extraction yield, polysaccharide content, polysaccharide molecular weight distribution and amount of water used for extraction are listed in Table 1.

Example 11

1) 1.5 kg dry, clean and mechanically pulverized lucid ganoderma sporocarp is put in an extraction container, 10 L ethanol is added, the mixer is heated until reflux to extract for 1 h, and the above procedure is repeated once;
2) Filtration is conducted, the filtrate is distilled under reduced pressure to recover ethanol, as to obtain a alcohol extract rich in liposoluble active components including triterpene, and the filtration residue is dried at 60-80° C. for further process;
3) The dry filtration residue in the step 2) is placed in a travelling wave microwave reaction chamber;
4) 300 g oxalic acid is added with water to prepare 10% oxalic acid solution;
5) 3 L oxalic acid solution of the step 4) is added into above mentioned microwave reaction chamber, and the mixer is sufficiently stirred to evenly wet the material;
6) Above mentioned mixer is subjected to irradiation at 6 KW continuous microwave power until the liquid refluxes, i.e., the organic acid solution is vaporized, and then the microwave is switched to a pulsed microwave power operating mode, wherein the duty ratio is 5 seconds/5 seconds (i.e. the ratio of on-time and off-time), peak power is 8 KW; after 15 min, vacuuming is conducted (reaction chamber working pressure is 20 mmHg) until no liquid is in the microwave reaction chamber;

7) 5 L absolute ethanol is added into lucid ganoderma sporocarp treated by microwave in the step 6), sufficiently stirred, and filtered, wherein the filtrate is distilled to recover ethanol, and the filtration residue after being dried is microwave treated lucid ganoderma sporocarp;

8) 100 g microwave treated lucid ganoderma sporocarp of the step 7) is placed in a 1 L beaker, 800 ml distill water is added thereinto, and the mixer is placed in a hot water bath at 70° C. for 40 min for extraction and then filtered. The above procedure is repeated once. The two filtrates are combined;

9) The filtrate after being concentrated is subjected to alcohol precipitation, and the precipitate is dried to obtain crude active polysaccharides;

10) 5 g crude active polysaccharides obtained in the step 9) is placed in a 100 ml beaker;

11) 50 ml distill water is added into the beaker of the step 10) and stirred for 30 mins;

12) The solution obtained in the step 11) is centrifuged at a RPM of 5000 r/min, the precipitate is discarded and the supernatant is remained;

13) The supernatant obtained in the step 12) is added into a dialysis bag (3000 m.w. cutoff) and is dialyzed in distilled water for 24 h;

14) The solution in the dialysis bag of the step 13) is taken out and is lyophilized in a lyophilizer to obtain refined polysaccharides;

15) Data including polysaccharide extraction yield, polysaccharide content, polysaccharide molecular weight distribution and amount of water used for extraction are listed in Table 1.

Example 12

1) 1.5 kg dry, clean and mechanically pulverized poria is put in an extraction container, 10 L ethanol is added, the mixer is heated until reflux to extract for 1 h, and the above procedure is repeated once;

2) Filtration is conducted, the filtrate is distilled under reduced pressure to recover ethanol, as to obtain a alcohol extract rich in liposoluble active components including triterpene, and the filtration residue is dried at 60-80° C. for further process;

3) The dry filtration residue in the step 2) is placed in a travelling wave microwave reaction chamber;

4) 2.8 L formic acid is added with water to prepare 80% formic acid solution;

5) 3 L formic acid solution of the step 4) is added into above mentioned microwave reaction chamber, and the mixer is sufficiently stirred to evenly wet the material;

6) Above mentioned mixer is subjected to irradiation at 6 KW continuous microwave power until the liquid refluxes, i.e., the organic acid solution is vaporized, and then the microwave is switched to a pulsed microwave power operating mode, wherein the duty ratio is 5 seconds/5 seconds (i.e. the ratio of on-time and off-time), peak power is 10 KW; after 20 min, vacuuming is conducted (reaction chamber working pressure is 20 mmHg) until no liquid is in the microwave reaction chamber;

7) 5 L absolute ethanol is added into poria treated by microwave in the step 6), sufficiently stirred, and filtered, wherein the filtrate is distilled to recover ethanol, and the filtration residue after being dried is microwave treated poria;

8) 100 g microwave treated poria of the step 7) is placed in a 1 L beaker, 800 ml distill water is added thereinto, and the mixer is placed in a hot water bath at 70° C. for 40 min for extraction and then filtered. The above procedure is repeated once. The two filtrates are combined;

9) The filtrate after being concentrated is subjected to alcohol precipitation, and the precipitate is dried to obtain active polysaccharides;

10) Data including polysaccharide extraction yield, polysaccharide content, polysaccharide molecular weight distribution and amount of water used for extraction are listed in Table 1.

Example 13

1) dry, clean and mechanically pulverized exidia auricula judae is put in an extraction container;

2) 2.8 L acetic acid is added with water to prepare 85% acetic acid solution;

3) 3 L acetic acid solution of the step 2) is added into above mentioned microwave reaction chamber, and the mixer is sufficiently stirred to evenly wet the material;

4) Above mentioned mixer is subjected to irradiation at 4 KW continuous microwave power until the liquid refluxes, i.e., the organic acid solution is vaporized, and then the microwave is switched to a pulsed microwave power operating mode, wherein the duty ratio is 5 seconds/5 seconds (i.e. the ratio of on-time and off-time), peak power is 6 KW; after 15 min, vacuuming is conducted (reaction chamber working pressure is 20 mmHg) until no liquid is in the microwave reaction chamber;

5) 5 L absolute ethanol is added into exidia auricula judae treated by microwave in the step 4), sufficiently stirred, and filtered, wherein the filtrate is distilled to recover ethanol, and the filtration residue after being dried is microwave treated exidia auricula judae;

6) 100 g microwave treated exidia auricula judae of the step 5) is placed in a 1 L beaker, 500 ml distill water is added thereinto, and the mixer is placed in a hot water bath at 70° C. for 40 min for extraction and then filtered. The above procedure is repeated once. The two filtrates are combined;

7) The filtrate after being concentrated is subjected to alcohol precipitation, and the precipitate is dried to obtain active polysaccharides;

8) Data including polysaccharide extraction yield, polysaccharide content, polysaccharide molecular weight distribution and amount of water used for extraction are listed in Table 1.

Example 14

1) dry, clean and mechanically pulverized mushroom sporocarp is put in an extraction container;

2) 3 L propionic acid is added with water to prepare 90% propionic acid solution;

3) 3 L propionic acid solution of the step 2) is added into above mentioned microwave reaction chamber, and the mixer is sufficiently stirred to evenly wet the material;

4) Above mentioned mixer is subjected to irradiation at 6 KW continuous microwave power until the liquid refluxes, i.e., the organic acid solution is vaporized, and then the microwave is switched to a pulsed microwave power operating mode, wherein the duty ratio is 5 seconds/5 seconds (i.e. the ratio of on-time and off-time), peak power is 8 KW; after 20 min, vacuuming is conducted (reaction chamber working pressure is 20 mmHg) until no liquid is in the microwave reaction chamber;
5) 5 L absolute ethanol is added into mushroom sporocarp treated by microwave in the step 4), sufficiently stirred, and filtered, wherein the filtrate is distilled to recover ethanol, and the filtration residue after being dried is microwave treated mushroom sporocarp;
6) 100 g microwave treated mushroom sporocarp of the step 5) is placed in a 1 L beaker, 600 ml distill water is added thereinto, and the mixer is placed in a hot water bath at 70° C. for 40 min for extraction and then filtered. The above procedure is repeated once. The two filtrates are combined;
7) The filtrate after being concentrated is subjected to alcohol precipitation, and the precipitate is dried to obtain active polysaccharides;
8) Data including polysaccharide extraction yield, polysaccharide content, polysaccharide molecular weight distribution and amount of water used for extraction are listed in Table 1.

TABLE 1

Polysaccharide product extraction yield, polysaccharide content, and amount of water used for polysaccharide extraction in Example 1-14.

| Example | Polysaccharide yield (wt) | Polysaccharide content (wt) | Polysaccharide molecular weight distribution | Acid used (liquid/solid) | Processing time (min) |
|---|---|---|---|---|---|
| Example1 | 10.2% | 73% | 3000-40000 | 2/1 | 15 |
| Example2 | 6.4% | 44% | 3000-20000 | 2/1 | 25 |
| Example3 | 35.4% | 92% | 3000-20000 | 2/1 | 20 |
| Example4 | 6.5% | 53% | 5000-12000 | 2/1 | 15 |
| Example5 | 8.4% | 79% | 4000-20000 | 2/1 | 15 |
| Example6 | 18.5% | 86% | 4000-30000 | 2/1 | 20 |
| Example7 | 9.6% | 54% | 3000-20000 | 2/1 | 15 |
| Example8 | 11.8% | 50% | 3000-20000 | 2/1 | 15 |
| Example9 | 12.5% | 63% | 5000-25000 | 2/1 | 20 |
| Example10 | 10.8% | 68% | 3000-25000 | 2/1 | 25 |
| Example11 | Crude polysaccharides 8.3% | 78% | 3000-12000 | 2/1 | 15 |
|  | Refined polysaccharides 5.4% | 94% | 3000-12000 |  |  |
| Example12 | 28.5% | 97% | 2000-8000 | 2/1 | 20 |
| Example13 | 15.0% | 72% | 5000-40000 | 2/1 | 15 |
| Example14 | 14.2% | 64% | 3000-15000 | 2/1 | 20 |

Experiment 1

Anti-Tumor Pharmaceutical Efficacy of Active Ingredient of Lucid Ganoderma Polysaccharides Experimental materials: lucid ganoderma polysaccharides, 78% crude polysaccharides and 94% purified polysaccharides, prepared in Example 11.

Experimental animals: Kunming mice, male, weight (22±2) g, provided by the Experimental Animal Center of Military Medical Sciences, Beijing Tumor lines: Lewis lung tumor lines and S180 sarcoma tumor lines, purchased from Shanghai Institutes for Biological Sciences.

Main instruments: DSX-280A Autoclave, produced by Shanghai Shen An Med Instrument; LD5-2A low-speed centrifuge, produced by Beijing Medical Centrifuge Company; 14ZQ-F160 thermostatic oscillator, produced by Harbin Donglian Electronic Technology Development Co., Ltd.

Experiment method: well growing tumor-bearing mice were sacrificed 7 days after being inoculated Lewis lung tumor and S180 sarcoma tumor. Well grown tumor tissues are selected to prepare cell suspension which is inoculated into the armpit of test mice, inoculation amount is 0.2 ml/mice, as to prepare focal solid tumor models. Inoculated mice are randomly divided into control group, positive control group, polysaccharide dose group, 10 mice/group. Mice are administrated with drugs 24 h after being inoculated with tumor cell, drugs are chronically intraperitoneal injected for 9 days, mice are weighed 24 h after the last administration, and sacrificed by cervical dislocation, and tumor is stripped and weighed.

Tumor inhibition rate is calculated as: Tumor inhibition rate (%)=(average tumor weight of the model group−average tumor weight of the drug administered group)/average tumor weight of the model group×100.

The results are in the table below:

| Polysaccharide sample | | | | |
|---|---|---|---|---|
| Purity | Tumor model | Dose (mg/kg) | Administration method | Tumor inhibition rate % |
| 78% | Lewis lung tumor | 200 | ip | 63.2 |
|  |  | 100 |  | 54 |
| 94% | Lewis lung tumor | 200 | ip | 60.1 |
|  |  | 100 |  | 53.2 |
| 78% | S180 | 200 | ip | 53.5 |
|  |  | 100 |  | 47.3 |
| 94% | S180 | 200 | ip | 47.6 |
|  |  | 100 |  | 41.2 |

It found that lucid ganoderma polysaccharides can effectively inhibit tumor growth.

The experiment results showed that, the present invention uses microwave chemistry method to treat flowers, leaves, fruits, seeds, barks, roots or tubers of common higher plants and mycelium or sporocarp of common fungi, then applies water extraction and alcohol precipitation methods to obtain water soluble polysaccharides, and overcomes shortcomings in the prior art like heavy water consumption, heavy energy consumption, low product yield, etc. Higher plants and fungi contain active polysaccharides as well as many other active components including triterpenes, flavonoids, saponins, etc. which may be alcohol extracted or water extracted respectively before or after the microwave treatment according to their differences in solubility from the polysaccharides, as to achieve comprehensive utilization of active ingredients in higher plants and fungi.

The invention claimed is:

1. A process of extracting higher plants or fungi polysaccharides based on a microwave chemistry treatment, comprising the following steps:
   a) treating pulverized higher plants or fungi with an organic solvent to remove liposoluble components thereof, to obtain higher plants or fungi residue; or directly using pulverized higher plants or fungi;

b) putting the residue or pulverized higher plants or fungi obtained in the step a) into a microwave reaction chamber, adding an acid solution of a mass concentration of 5% to 99% to the reaction chamber, subjecting a mixture of the residue or pulverized higher plants or fungi and the acid solution for 5 to 120 minutes to a microwave power of mass power density of 1 kilowatt per kilogram of material to 10 kilowatts per kilogram of material under a work pressure of 20 mmHg to 760 mmHg; and then washing with an organic solvent to remove excess acid; and c) conducting extraction by adding water solution of 5 to 15 times by volume into the product obtained from the step b), subjecting the extraction solution to alcohol precipitation to form precipitates, separating the precipitates containing the polysaccharides.

2. The process of claim 1, wherein, the application method of the microwave power in said step b) is a continuous microwave mode or a combination of continuous microwave and pulse microwave modes; wherein, in case of using the combination of continuous microwave and pulse microwave, the continuous microwave irradiation is first used until the acid solution refluxes, and then is switched to pulse microwave for 5 to 120 minutes.

3. The process of claim 1, further comprising concentrating the mixture before washing the mixture with the organic solvent in step b), wherein the acid solution is a volatile acid, and wherein the acid is removed during concentrating the mixture.

4. The process of claim 2, wherein, in said step b), in case of continuous microwave, mass power density is 1 kilowatt per kilogram of material to 5 kilowatts per kilogram of material; in case of pulse microwave, mass power density is 2 kilowatts per kilogram of material to 10 kilowatts per kilogram of material, the duty ratio is A/B, where A is on-time and B is off-time, and A=1 sec to 100 sec, B=1 sec to 100 sec.

5. The process of claim 2, wherein, the acid solution in said step b) is an organic acid or a mixed solution of an organic acid and an inorganic acid.

6. The process of claim 5, wherein, the organic acid solution in said step b) is selected from the group consisting of oxalic acid, formic acid, acetic acid, and propionic acid.

7. The process of claim 6, wherein, in said step b) a weight percentage concentration of oxalic acid is 5% to 50%; a weight percentage concentration of formic acid is 10% to 99%; a weight percentage concentration of acetic acid is 10% to 99%; or a weight percentage concentration of propionic acid is 10% to 99%.

8. The process of claim 5, wherein, in the mixed solution of an organic acid and an inorganic acid used in said step b), the mass percentage concentration of the inorganic acid in the mixed solution is 0.1% to 15%.

9. The process of claim 8, wherein, the inorganic acid in the step b) is selected from hydrochloric acid, sulfuric acid, nitric acid or phosphoric acid.

10. The process of claim 1, wherein, in the step b), the ratio of the residue or pulverized higher plants or fungi obtained in step a) to the amount of the acid solution is 5/1 to 1/5.

11. The process of claim 1, wherein, the organic solvent used in said step b) is selected from methanol, ethanol, propanol or acetone.

12. The process of claim 1, wherein, the organic solvent used in said step a) is petroleum ether, methanol, ethanol, propanol or ethyl acetate.

13. The process of claim 1, wherein, the liposoluble component in the step a) is volatile oils, flavonoids, triterpenoids or saponins.

14. The process of claim 1, wherein, the alcohol used in said step c) is ethanol.

15. The process of claim 1, wherein, the higher plants is selected from flowers, leaves, seeds, barks, fruits, roots or tubers raw materials of *astragalus*, wolfberry, ginko leaf, *papaya*, honeysuckle, Chinese *angelica*, orange peel, *ephedra sinica, ligusticum* chuanxiong hort, *acorus gramineus*, garlic, sharpleaf galangal fruit, *angelica*, Chinese mugwort leaf, *asarum, cistanche, elaeagnus angustifolia, eucalyptus* leaf, *cordata, ligustrum lucidum, notopterygium, ginseng, panax pseudoginseng, sarcandra glabra, plantago, polygonum orientale* fruit, *daphne genkwa*, bergamot, white mulberry root-bark, mistletoe, *scutellaria baicalensis, epimedium*, tea leaf, *rhodiola, aloe*, oat, konjac, yam, *gastrodia elata, radix bupleuri* or *acanthopanax*; the fungi is selected from fungal sporocarp or mycelium of lucid *ganoderma, exidia auricula judae*, mushrooms, polyporus, tremella, maitake, *poria*, rainbow conk, *hericium erinaceus* or *cordyceps sinensis*.

16. The process of claim 15, wherein, the higher plants is *astragalus*, wolfberry, yam, gingko leaf, *panax pseudoginseng, plantago, gastrodia elata, eucommia ulmoides, salvia* or kudzu; the fungi is lucid *ganoderma, poria, exidia auricula judae*, or mushrooms.

17. The process of claim 1, wherein, the process of preparing *astragalus* polysaccharides comprising:
pulverizing *astragalus* and degreasing the *astragalus* with ethanol;
putting the *astragalus* into a microwave extraction chamber, adding 10% to 35% oxalic acid solution of 1.5 to 2.5 times of the weight thereof to the extraction chamber, at a microwave power density 1 to 2 KW/Kg under 500 mmHg to 760 mmHg pressure maintaining a reflux of oxalic acid solution for 15 to 30 minutes, and then evaporating under reduced pressure the liquid in the microwave extraction chamber to dryness;
adding an ethanol solution of 3 to 5 times of the weight of the *astragalus* to the reaction chamber, stirring and washing for 40 to 60 minutes, and conducting filtration;
drying filtration residue and extracting the filtration residue after being dried twice with water, wherein each time the amount of water is 6 to 8 times of the weight of the residue, the extraction temperature is 70° C., and the extraction time is about 40 minutes;
conducting filtration, combining the two filtrate solutions, and concentrating the filtrate solution to a volume of 1/5 of the original extracting solution; and
adding ethanol for precipitation, and drying precipitates to obtain *astragalus* polysaccharides.

18. The process of claim 17, wherein, the molecular weight distribution of said prepared *astragalus* polysaccharide is 3000 to 40000.

19. The process of claim 1, wherein, the process of preparing wolfberry polysaccharides, comprising:
degreasing wolfberry petroleum ether or ethanol;
putting the wolfberry into a microwave extraction chamber, adding 30% to 85% formic acid solution of 1 to 2.5 times of the weight thereof to the extraction chamber, at a microwave power density 1 to 2 KW/Kg under 500 mmHg to 760 mmHg pressure maintaining a reflux of formic acid solution for 15 to 25 minutes, and then evaporating under reduced pressure the formic acid to dryness;

adding an ethanol solution of 3 to 5 times of the weight of the wolfberry to the reaction chamber, stirring and washing for 40 to 60 minutes and conducting filtration;

drying filtration residue and extracting the filtration residue after being dried twice with water, wherein each time the amount of water is 6 to 8 times of the weight of the residue, the extraction temperature is 70° C., and the extraction time is about 40 minutes;

conducting filtration, combining the two filtrate solutions, and concentrating the filtrate solution to a volume of 1/5 of the original extracting solution; and adding ethanol for precipitation, and drying precipitates to obtain wolfberry polysaccharides.

20. The process of claim 19, wherein, the molecular weight distribution of said prepared wolfberry polysaccharide is 3000 to 20000.

21. The process of claim 1, wherein, the process of preparing yam polysaccharides comprising:

pulverizing yam;

putting the yam into a microwave extraction chamber, adding 70% to 95% propionic acid solution of 1.5 to 2.5 times of the weight thereof to the extraction chamber, at a microwave power density 1 to 2 KW/Kg under 500 mmHg to 760 mmHg pressure maintaining a reflux of propionic acid solution for 15 to 25 minutes, and then evaporating under reduced pressure the propionic acid to dryness;

adding ethanol solution of 3 to 5 times of the weight of the yam to the reaction chamber, stirring and washing for 40 to 60 minutes and conducting filtration;

drying filtration residue and extracting the filtration residue after being dried twice with water, wherein each time the amount of water is 6 to 8 times of the weight of the residue, the extraction temperature is 70° C., and the extraction time is about 40 minutes;

conducting filtration, combining the two filtrate solutions, and concentrating the filtrate solution to a volume of 1/5 of the original extracting solution; and adding ethanol for precipitation, and drying precipitates to obtain yam polysaccharides.

22. The process of claim 21, wherein the molecular weight distribution of said prepared yam polysaccharide is 3000 to 20000.

23. The process of claim 1, wherein, the process of preparing gingko polysaccharides comprising:

pulverizing gingko and degreasing the gingko with ethanol;

putting the gingko into a microwave extraction chamber, adding 30% to 85% formic acid solution of 1.5 to 2.5 times of the weight thereof to the extraction chamber, at a microwave power density 1 to 2 KW/Kg under 500 mmHg to 760 mmHg pressure maintaining a reflux of formic acid solution for 15 to 25 minutes, and then evaporating under reduced pressure the formic acid to dryness;

adding an ethanol solution of 4 to 6 times of the weight of the gingko to the reaction chamber, stirring and washing for 40 to 60 minutes and conducting filtration;

drying filtration residue and extracting the filtration residue after being dried twice with water, wherein each time the amount of water is 6 to 8 times of the weight of the residue, the extraction temperature is 70° C., and the extraction time is about 40 minutes;

conducting filtration, combining two filtrate solutions, and concentrating the filtrate solution to a volume of 1/5 of the original extracting solution; and adding ethanol for precipitation, and drying precipitates to obtain gingko polysaccharides.

24. The process of claim 23, wherein the molecular weight distribution of said prepared gingko polysaccharide is 5000 to 12000.

25. The process of claim 1, wherein, the process of preparing *panax pseudoginseng* polysaccharides, comprising:

pulverizing *panax pseudoginseng* and degreasing the *panax pseudoginseng* with ethanol;

putting the *panax pseudoginseng* into a microwave extraction chamber, adding 60% to 95% acetic acid solution of 1.5 to 2.5 times of the weight thereof to the extraction chamber, at a microwave power density 1 to 2 KW/Kg under 500 mmHg to 760 mmHg pressure maintaining a reflux of acetic acid solution for 15 to 25 minutes, and then evaporating under reduced pressure the acetic acid to dryness;

adding an ethanol solution of 3 to 5 times of the weight of the *panax pseudoginseng* to the reaction chamber, stirring and washing for 40 to 60 minutes and conducting filtration;

drying filtration residue and extracting the filtration residue after being dried twice with water, wherein each time the amount of water is 6 to 8 times of the weight of the residue, the extraction temperature is 70° C., and the extraction time is about 40 minutes;

conducting filtration, combining two filtrate solutions, and concentrating the filtrate solution to a volume of 1/5 of the original extracting solution; and adding ethanol for precipitation, and drying precipitates to obtain *panax pseudoginseng* polysaccharides.

26. The process of claim 25, wherein the molecular weight distribution of said prepared *panax pseudoginseng* polysaccharide is 4000 to 20000.

27. The process of claim 1, wherein, the process of preparing *plantago* polysaccharides, comprising:

degreasing *plantago* with petroleum ether or ethanol;

putting the *plantago* into a microwave extraction chamber, adding 80% to 95% propionic acid solution of 1.5 to 2.5 times of the weight thereof to the extraction chamber, at a microwave power density 1 to 2 KW/Kg under 500 mmHg to 760 mmHg pressure maintaining a reflux of propionic acid solution for 15 to 25 minutes, and then evaporating under reduced pressure the propionic acid to dryness;

adding an ethanol solution of 3 to 5 times of the weight of the *plantago* to the reaction chamber, stirring and washing for 40 to 60 minutes and conducting filtration;

drying filtration residue and extracting the filtration residue after being dried twice with water, wherein each time the amount of water is 6 to 8 times of the weight of the residue, the extraction temperature is 70° C., and the extraction time is about 40 minutes;

conducting filtration and combining two filtrate solutions, and concentrating the filtrate solution to a volume of 1/5 of the original extracting solution; and adding ethanol for precipitation, and drying precipitates to obtain *plantago* polysaccharides.

28. The process of claim 27, wherein the molecular weight distribution of said prepared *plantago* polysaccharide is 4000 to 30000.

29. The process of claim 1, wherein, the process of preparing *gastrodia elata* polysaccharides comprising:

pulverizing *gastrodia elata* and degrasing the *gastrodia elata* with ethanol;

putting the *gastrodia elata* into a microwave extraction chamber, adding a formic acid-hydrochloride acid mixed solution of 0.3% to 0.6% hydrochloride acid and 30% to 85% formic acid of 1.5 to 2.5 times of the weight thereof to the extraction chamber, at a microwave power density 1 to 2 KW/Kg under 500 mmHg to 760 mmHg pressure maintaining a reflux of the acids mixed solution for 15 to 25 minutes, and then evaporating under reduced pressure the acids mixed solution to dryness;

adding an ethanol solution of 3 to 5 times of the weight of the *gastrodia elata* to the reaction chamber, stirring and washing for 40 to 60 minutes and conducting filtration;

drying filtration residue and extracting the filtration residue after being dried twice with water, wherein each time the amount of water is 6 to 8 times of the weight of the residue, the extraction temperature is 70° C., and the extraction time is about 40 minutes;

conducting filtration combining two filtrate solutions, and concentrating the filtrate solution to a volume of 1/5 of the original extracting solution; and adding ethanol for precipitation, and drying precipitates to obtain *gastrodia elata* polysaccharides.

30. The process of claim 29, wherein the molecular weight distribution of said prepared *gastrodia elata* polysaccharides is 3000 to 20000.

31. The process of claim 1, wherein, the process of preparing *eucommia ulmoides* polysaccharides comprising:

pulverizing *eucommia ulmoides* and degreasing the *eucommia ulmoides* with ethanol;

putting *eucommia ulmoides* into a microwave extraction chamber, adding 30% to 85% formic acid solution of 1.5 to 2.5 times of the weight thereof to the extraction chamber, at a microwave power density 1 to 2 KW/Kg under 500 mmHg to 760 mmHg pressure maintaining a reflux of formic acid solution for 15 to 25 minutes, and then evaporating under reduced pressure the formic acid to dryness;

adding an ethanol solution of 3 to 5 times of the weight of the *eucommia ulmoides* to the reaction chamber, stirring and washing for 40 to 60 minutes and conducting filtration;

drying filtration residue and extracting the filtration residue after being dried twice with water, wherein each time the amount of water is 6 to 8 times of the weight of the residue, the extraction temperature is 70° C., and the extraction time is about 40 minutes;

conducting filtration and combining two filtrate solutions, and concentrating the filtrate solution to a volume of 1/5 of the original extracting solution; and adding ethanol for precipitation, and drying precipitates to obtain *eucommia ulmoides* polysaccharides.

32. The process of claim 31, wherein the molecular weight distribution of said prepared *eucommia ulmoides* polysaccharide is 3000 to 20000.

33. The process of claim 1, wherein, the process of preparing *salvia* polysaccharides comprising:

pulverizing *salvia* and degreasing the *salvia* with ethanol;

putting the *salvia* into a microwave extraction chamber, adding 60% to 95% acetic acid solution of 1.5 to 2.5 times of the weight thereof to the extraction chamber, at a microwave power density 1 to 2 KW/Kg under 500 mmHg to 760 mmHg pressure maintaining a reflux of acetic acid solution for 15 to 25 minutes, and then evaporating under reduced pressure the acetic acid to dryness;

adding an ethanol solution of 3 to 5 times of the weight of the *salvia* to the reaction chamber, stirring and washing for 40 to 60 minutes and conducting filtration;

drying filtration residue and extracting the filtration residue after being dried twice with water, wherein each time the amount of water is 6 to 8 times of the weight of the residue, the extraction temperature is 70° C., and the extraction time is about 40 minutes;

conducting filtration and combining two filtrate solutions, and concentrating the filtrate solution to a volume of 1/5 of the original extracting solution; and adding ethanol for precipitation, and drying precipitates to obtain *salvia* polysaccharides.

34. The process of claim 33, wherein the molecular weight distribution of said prepared *salvia* polysaccharides is 5000 to 25000.

35. The process of claim 1, wherein, the process of preparing kudzu polysaccharides comprising:

pulverizing kudzu and degreasing the kudzu with ethanol;

putting kudzu into a microwave extraction chamber, adding 70% to 95% propionic acid solution of 1.5 to 2.5 times of the weight thereof to the extraction chamber, at a microwave power density 1 to 2 KW/Kg under 500 mmHg to 760 mmHg pressure maintaining a reflux of propionic acid solution for 15 to 25 minutes, and then evaporating under reduced pressure the propionic acid to dryness;

adding an ethanol solution of 3 to 5 times of the weight of the kudzu to the reaction chamber, stirring and washing for 40 to 60 minutes and conducting filtration;

drying filtration residue and extracting the filtration residue after being dried twice with water, wherein each time the amount of water is 6 to 8 times of the weight of the residue, the extraction temperature is 70° C., and the extraction time is about 40 minutes;

conducting filtration and combining two filtrate solutions, and concentrating the filtrate solution to a volume of 1/5 of the original extracting solution; and adding ethanol for precipitation, and drying precipitates to obtain kudzu polysaccharides.

36. The process of claim 35, wherein the molecular weight distribution of said prepared kudzu polysaccharide is 3000 to 25000.

37. The process of claim 1, wherein, the process of preparing lucid *ganoderma* polysaccharides, comprising:

pulverizing lucid *ganoderma* sporocarp and degreasing the lucid *ganoderma* sporocarp with ethanol;

putting lucid *ganoderma* sporocarp into a microwave extraction chamber, adding 10% to 35% oxalic acid solution of 1.5 to 2.5 times of the weight thereof to the extraction chamber, at a microwave power density 1 to 2 KW/Kg under 500 mmHg to 760 mmHg pressure maintaining a reflux of oxalic acid solution for 15 to 25 minutes, and then evaporating under reduced pressure the liquid to dryness;

adding an ethanol solution of 3 to 5 times of the weight of the lucid *ganoderma* sporocarp to the reaction chamber, stirring and washing for 40 to 60 minutes and conducting filtration;

drying filtration residue and extracting the filtration residue after being dried twice with water, wherein each time the amount of water is 6 to 8 times of the weight of the residue, the extraction temperature is 70° C., and the extraction time is about 40 minutes;

conducting filtration and combining two filtrate solutions, and concentrating the filtrate solution to a volume of 1/5 of the original extracting solution; and adding ethanol for precipitation, and drying precipitates to obtain lucid *ganoderma* polysaccharides.

38. The process of claim 37, wherein the molecular weight distribution of said prepared lucid *ganoderma* polysaccharide is 3000 to 12000.

39. The process of claim 1, wherein, the process of preparing poria polysaccharides comprising:
    pulverizing poria and degreasing the poria with ethanol;
    putting poria into a microwave extraction chamber, adding 30% to 85% formic acid solution of 1.5 to 2.5 times of the weight thereof to the extraction chamber, at a microwave power density 1 to 2 KW/Kg under 500 mmHg to 760 mmHg pressure maintaining a reflux of formic acid solution for 15 to 25 minutes, and then evaporating under reduced pressure the formic acid to dryness;
    adding an ethanol solution of 3 to 5 times of the weight of the poria to the reaction chamber, stirring and washing for 40 to 60 minutes and conducting filtration;
    drying filtration residue and extracting the filtration residue after being dried twice with water, wherein each time the amount of water is 6 to 8 times of the weight of the residue, the extraction temperature is 70° C., and the extraction time is about 40 minutes;
    conducting filtration and combining two filtrate solutions, and concentrating the filtrate solution to a volume of 1/5 of the original extracting solution; and
    adding ethanol for precipitation, and drying precipitates to obtain poria polysaccharides.

40. The process of claim 39, wherein the molecular weight distribution of said prepared poria polysaccharides is 2000 to 8000.

41. The process of claim 1, wherein, the process of preparing *exidia auricula judae* polysaccharides comprising:
    pulverizing *exidia auricula judae*;
    putting the *exidia auricula judae* into a microwave extraction chamber, adding 60% to 95% acetic acid solution of 1.5 to 2.5 times of the weight thereof to the extraction chamber, at a microwave power density 1 to 2 KW/Kg under 500 mmHg to 760 mmHg pressure maintaining a reflux of acetic acid solution for 15 to 25 minutes, and then evaporating under reduced pressure the acetic acid to dryness;
    adding an ethanol solution of 3 to 5 times of the weight of the *exidia auricula judae* to the reaction chamber, stirring and washing for 40 to 60 minutes and conducting filtration;
    drying filtration residue and extracting the filtration residue after being dried twice with water, wherein each time the amount of water is 6 to 8 times of the weight of the residue, the extraction temperature is 70° C., and the extraction time is about 40 minutes;
    conducting filtration and combining two filtrate solutions, and concentrating the filtrate solution to a volume of 1/5 of the original extracting solution; and
    adding ethanol for precipitation, and drying precipitates to obtain *exidia auricula judae* polysaccharides.

42. The process of claim 41, wherein the molecular weight distribution of said prepared *exidia auricula judae* polysaccharide is 5000 to 40000.

43. The process of claim 1, wherein, the process of preparing mushroom polysaccharides comprising:
    pulverizing mushroom sporocarp;
    putting the mushroom sporocarp into a microwave extraction chamber, adding 70% to 95% propionic acid solution of 1.5 to 2.5 times of the weight thereof to the extraction chamber, at a microwave power density 1 to 2 KW/Kg under 500 mmHg to 760 mmHg pressure maintaining a reflux of propionic acid solution for 15 to 25 minutes, and then evaporating under reduced pressure the propionic acid to dryness;
    adding an ethanol solution of 3 to 5 times of the weight of the mushroom to the reaction chamber, stirring and washing for 40 to 60 minutes and conducting filtration;
    drying filtration residue and extracting the filtration residue after being dried twice with water, wherein each time the amount of water is 6 to 8 times of the weight of the residue, the extraction temperature is 70° C., and the extraction time is about 40 minutes;
    conducting filtration and combining two filtrate solutions, and concentrating the filtrate solution to a volume of 1/5 of the original extracting solution; and
    adding ethanol for precipitation, and drying precipitates to obtain mushroom polysaccharides.

44. The process of claim 43, wherein the molecular weight distribution of said prepared mushroom polysaccharide is 3000 to 15000.

* * * * *